(12) United States Patent
Cartledge et al.

(10) Patent No.: US 7,044,910 B2
(45) Date of Patent: May 16, 2006

(54) MODIFIED LARYNGOSCOPE BLADE TO REDUCE DENTAL INJURIES DURING INTUBATION

(75) Inventors: Richard Cartledge, New York, NY (US); Joshua Lane, Augusta, GA (US)

(73) Assignee: Cartledge Medical Products, Inc., Hollywood, FL (US)

( * ) Notice: Subject to any disclaimer, the term of this patent is extended or adjusted under 35 U.S.C. 154(b) by 246 days.

(21) Appl. No.: 10/639,369

(22) Filed: Aug. 12, 2003

(65) Prior Publication Data

US 2004/0034281 A1 Feb. 19, 2004

Related U.S. Application Data

(62) Division of application No. 09/911,257, filed on Jul. 23, 2001, now Pat. No. 6,623,425.

(51) Int. Cl.
*A61B 1/267* (2006.01)
(52) U.S. Cl. .................. 600/195; 600/190; 600/185
(58) Field of Classification Search ............... 600/190, 600/194, 195, 186, 185
See application file for complete search history.

(56) References Cited

U.S. PATENT DOCUMENTS

| | | | |
|---|---|---|---|
| 3,507,272 A | 4/1970 | Laerdal |
| 3,595,222 A | 7/1971 | Vellacott et al. |
| 3,598,113 A | 8/1971 | Moore et al. |
| 3,643,654 A | 2/1972 | Felbarg |
| 3,766,909 A | 10/1973 | Ozbey |
| 3,826,248 A | 7/1974 | Gobels |
| 3,856,001 A | 12/1974 | Phillips |
| 3,874,093 A | 4/1975 | Garbe |
| 3,943,920 A | 3/1976 | Kandel |
| 4,086,919 A | 5/1978 | Bullard |
| 4,112,933 A | 9/1978 | Moses |
| 4,114,609 A | 9/1978 | Moses |
| 4,126,127 A | 11/1978 | May |
| 4,295,465 A | 10/1981 | Racz et al. |
| 4,306,547 A | 12/1981 | Lowell |
| 4,314,551 A | 2/1982 | Kadell |
| 4,320,745 A | 3/1982 | Bhitiyakul et al. |
| 4,337,761 A | 7/1982 | Upsher |
| 4,360,008 A | 11/1982 | Corazzelli, Jr. |
| 4,384,570 A | 5/1983 | Roberts |
| 4,425,909 A | 1/1984 | Rieser |

(Continued)

FOREIGN PATENT DOCUMENTS

EP 0 110 333 A2 6/1984

(Continued)

*Primary Examiner*—Beverly M. Flanagan
(74) *Attorney, Agent, or Firm*—Troutman Sanders LLP; Ralph E. Gaskins, Jr.

(57) ABSTRACT

The present invention relates to the field of medical devices used in the procedures of orotracheal or nasotracheal intubation. Oral or nasal endotracheal intubation procedures are commonly employed to secure a controlled airway and to deliver inhalant oxygen, anesthetic gases, and other therapeutic agents into the trachea and lungs of human and veterinary patients. Such intubation procedures carry a significant risk of dental injury resulting from contact between the laryngoscope blade used for visualization during intubation. The present invention provides an apparatus to reduce dental injury including a modified laryngoscope blade and a disposable insert which is designed to be received and retained in a single step by the modified laryngoscope blade. The disposable insert may be quickly secured by the user, and reduces both direct pressure and shear forces on the maxillary incisor teeth when the laryngoscope blade is placed in a patient's mouth during intubation.

27 Claims, 5 Drawing Sheets

U.S. PATENT DOCUMENTS

| | | |
|---|---|---|
| 4,432,350 A | 2/1984 | Breslau et al. |
| 4,437,458 A | 3/1984 | Upsher |
| 4,517,964 A | 5/1985 | Upsher |
| 4,527,553 A | 7/1985 | Upsher |
| 4,557,256 A | 12/1985 | Bauman |
| 4,570,614 A | 2/1986 | Bauman |
| 4,573,451 A | 3/1986 | Bauman |
| 4,574,784 A | 3/1986 | Soloway |
| 4,579,108 A | 4/1986 | Bauman |
| 4,583,527 A | 4/1986 | Musicant et al. |
| 4,592,343 A | 6/1986 | Upsher |
| 4,607,623 A | 8/1986 | Bauman |
| 4,669,449 A | 6/1987 | Bauman |
| 4,694,822 A | 9/1987 | Bauman |
| 4,705,024 A | 11/1987 | Bainton |
| 4,729,367 A | 3/1988 | Bauman |
| D297,363 S | 8/1988 | Salerno |
| 4,815,451 A | 3/1989 | Bauman |
| 4,827,910 A | 5/1989 | Matthews, III |
| 4,878,486 A | 11/1989 | Slater |
| 4,884,558 A | 12/1989 | Gorski et al. |
| 4,901,708 A | 2/1990 | Lee |
| 4,905,669 A | 3/1990 | Bullard et al. |
| 4,924,855 A | 5/1990 | Salerno et al. |
| 4,930,495 A | 6/1990 | Upsher |
| 4,947,829 A | 8/1990 | Bullard |
| 4,947,896 A | 8/1990 | Bartlett |
| 4,958,624 A | 9/1990 | Stone et al. |
| D312,308 S | 11/1990 | Abadir |
| D312,500 S | 11/1990 | Abadir |
| 4,982,729 A | 1/1991 | Wu |
| 5,003,962 A | 4/1991 | Choi |
| D316,898 S | 5/1991 | Park |
| 5,033,480 A | 7/1991 | Wiley et al. |
| 5,036,835 A | 8/1991 | Filli |
| 5,060,633 A | 10/1991 | Gibson |
| 5,063,907 A | 11/1991 | Musicant et al. |
| 5,065,738 A | 11/1991 | Van Dam |
| 5,070,859 A | 12/1991 | Waldvogel |
| 5,092,314 A | 3/1992 | Zeitels |
| 5,093,079 A | 3/1992 | Bakaitis et al. |
| 5,095,888 A | 3/1992 | Hawley |
| 5,178,131 A | 1/1993 | Upsher |
| 5,178,132 A | 1/1993 | Mahefky |
| 5,184,603 A | 2/1993 | Stone |
| D337,384 S | 7/1993 | Schucman |
| 5,261,392 A | 11/1993 | Wu |
| 5,263,472 A | 11/1993 | Ough |
| 5,277,173 A | 1/1994 | Cantele |
| 5,347,995 A | 9/1994 | Slater et al. |
| 5,349,943 A | 9/1994 | Ruiz |
| 5,355,870 A | 10/1994 | Lacy |
| 5,363,838 A | 11/1994 | George |
| 5,363,840 A | 11/1994 | Silva |
| 5,381,787 A | 1/1995 | Bullard |
| 5,406,941 A | 4/1995 | Roberts |
| 5,425,356 A | 6/1995 | Ough |
| 5,438,976 A | 8/1995 | Nash |
| 5,443,058 A | 8/1995 | Ough |
| 5,498,231 A | 3/1996 | Franicevic |
| 5,501,651 A | 3/1996 | Bauman |
| D369,407 S | 4/1996 | Smith |
| 5,536,245 A | 7/1996 | Dahlbeck |
| 5,542,905 A | 8/1996 | Nussenbaum |
| 5,551,946 A | 9/1996 | Bullard |
| 5,571,071 A | 11/1996 | Shapiro |
| 5,575,758 A | 11/1996 | Easterbrook, III |
| 5,584,795 A | 12/1996 | Valenti |
| 5,603,688 A | 2/1997 | Upsher |
| 5,651,760 A | 7/1997 | Upsher |
| 5,651,761 A | 7/1997 | Upsher |
| 5,702,351 A | 12/1997 | Bar-Or et al. |
| 5,743,849 A | 4/1998 | Rice et al. |
| 5,772,581 A | 6/1998 | Gaines |
| 5,776,052 A | 7/1998 | Callahan |
| 5,776,053 A | 7/1998 | Dragisic et al. |
| D399,957 S | 10/1998 | Chernov et al. |
| 5,827,178 A | 10/1998 | Berall |
| 5,846,186 A | 12/1998 | Upsher |
| 5,873,818 A | 2/1999 | Rothfels |
| 5,879,304 A | 3/1999 | Shuchman et al. |
| 5,888,195 A | 3/1999 | Schneider |
| 5,938,591 A | 8/1999 | Minson |
| D413,977 S | 9/1999 | Cranton et al. |
| 5,984,863 A | 11/1999 | Ansari |
| 5,993,383 A | 11/1999 | Haase |
| 6,013,026 A | 1/2000 | Krauter et al. |
| 6,036,639 A | 3/2000 | Allred, III et al. |
| 6,090,040 A | 7/2000 | Metro |
| 6,095,972 A | 8/2000 | Sakamoto |
| 6,102,851 A | 8/2000 | Mellin |
| 6,106,458 A | 8/2000 | Ha |

FOREIGN PATENT DOCUMENTS

| | | |
|---|---|---|
| EP | 0 169 497 A2 | 1/1986 |
| EP | 0 233 761 A2 | 8/1987 |
| EP | 0 338 073 B1 | 10/1989 |
| EP | 0 339 541 A1 | 11/1989 |
| EP | 0 500 778 B1 | 9/1992 |
| EP | 0 586 972 A1 | 3/1994 |
| EP | 0 586 972 B1 | 3/1994 |
| EP | 1 025 796 A1 | 8/2000 |
| WO | WO 89/02719 | 4/1989 |
| WO | WO 91/07201 | 5/1991 |
| WO | WO 97/30626 | 8/1997 |
| WO | WO 97/46169 | 12/1997 |
| WO | WO 98/19589 | 5/1998 |
| WO | WO 99/18841 | 4/1999 |
| WO | WO 99/29228 | 6/1999 |
| WO | WO 99/48416 | 9/1999 |

Fig. 11

MODIFIED LARYNGOSCOPE BLADE TO REDUCE DENTAL INJURIES DURING INTUBATION

CROSS-REFERENCE TO RELATED APPLICATION

The present application is a divisional of U.S. patent application Ser. No. 09/911,257 filed Jul. 23, 2001, now U.S. Pat. No. 6,623,425.

FIELD OF THE INVENTION

The present invention relates to the field of medical devices used in the procedures of orotracheal or nasotracheal intubation. More particularly, the present invention relates to a modified laryngoscope blade which is designed to receive a disposable insert which reduces both direct pressure and shear forces on the maxillary incisor teeth when the laryngoscope blade is placed in a patient's mouth during intubation.

BACKGROUND OF THE INVENTION

Oral or nasal endotracheal intubation procedures are commonly employed to secure a controlled airway and to deliver inhalant oxygen, anesthetic gases, and other therapeutic agents into the trachea and lungs of human and veterinary patients. These clinical procedures are usually performed as a preliminary measure before surgery, thus enabling the anesthesiologist to administer anesthetic gases and other drugs while maintaining a stable delivery of oxygen to the patient's lungs throughout the surgical procedure. In other settings, intubation is used to provide a patient with a secure, direct airway when mechanical ventilation of the patient is indicated.

The conventional procedure for such intubation procedures involves the visualization of the glottis and adjacent anatomic areas with a laryngoscope. A laryngoscope typically includes a handle containing a power supply and an attached blade section that serves to displace the tongue and allow direct visualization of the patient's larynx through the mouth. The technique of orotracheal or direct nasotracheal intubation involves sighting the vocal cords and the insertion of an endotracheal tube therethrough in a patient who is usually anesthetized or unconscious. The laryngoscope blade is usually introduced laterally through the right side of the mouth, and then directed medially to exclude and retract the tongue for adequate visualization of the hypopharynx.

Training and experience combine to make intubation a safe, effective, and atraumatic technique. For example, a safe approach to intubation in advance of a surgical procedure involves first providing the patient with a short-acting sedative and a skeletal muscle relaxant before initiating laryngoscopy. Then, the head, neck, and shoulders of the patient must be positioned so that the oral, pharyngeal, and laryngeal axes are optimally aligned. Finally, the laryngoscope is inserted, preferably with the laryngoscopist's left hand—without regard to whether the laryngoscopist is right or left handed-laterally from the right side of the patient's mouth to avoid the incisor teeth and the tongue is deflected away from the lumen of the pharyngeal outlet by the tip of the laryngoscope blade. The epiglottis is sighted above the base of the tongue and, according to the type of laryngoscope blade used, the instrument is manipulated to expose the glottic opening. The endotracheal tube is then introduced through either the mouth or nose, and visually advanced between the vocal cords into the subglottic space. Once placement has been achieved, the laryngoscope blade is carefully removed to avoid either injury to oropharyngeal structures or unintentional displacement of the endotracheal tube.

Many types of laryngoscope blades have been developed, each characterized by blade curvature or lack thereof, the point of such curvature if the blade is curved, and the flange structure of the blade. Three types of blades are most prominently used. An example of a first type of blade, characterized as a curved blade, is known in the art as the MacIntosh blade. The MacIntosh blade is advanced into the space between the base of the tongue and the pharyngeal surface of the epiglottis. Forward and upward movement of this blade stretches the hypoepiglottic ligament to cause the epiglottis to move upward to expose the glottic opening. Two other types of prominently used blades are the straight blade, known as the Jackson or Wisconsin blade, and the straight blade with a curved tip, known in the art as the Miller blade. The tip of these blades are passed beneath the laryngeal surface of the epiglottis and moved upwardly to elevate the epiglottis, thereby exposing the glottic opening.

During insertion of the laryngoscope, care must be taken to avoid pressure on the teeth and gums of the patient. Care must also be taken to avoid traumatizing both the oral mucosa and the epiglottis. Use of a gentle technique for inserting the laryngoscope, may lessen, but cannot totally remove the possibility of intubation trauma. However, poor dentition or suboptimal anatomy of the teeth, jaw, neck, or throat may leave the maxillary incisors at particularly significant risk during intubation by even the most experienced of technicians.

When properly positioned, a laryngoscope blade may rest against the upper teeth of the maxilla, depending upon the individual patient's anatomy. Because the laryngoscope blade is necessarily formed of a hard, inflexible material, dental damage is a potential result of such intubation procedures. Such dental injury is typically aggravated when the upper teeth are used as a fulcrum during insertion procedures.

Even edentulous patients may be at risk for significant injuries to their maxillary alveolar ridges during the process of endotracheal intubation. The same mechanism of injury that may fracture or dislocate teeth may contuse or fracture the maxillary alveolar ridge, resulting in post-intubation difficulties in using the patient's previous dental prostheses or dentures. Such prostheses may have to be replaced, at considerable cost. In addition, residual local pain at the site of injury may aggravate the patient's tolerance for the use of any dental prostheses following such an intubation injury.

Various methods have been proposed to minimize such dental injury. Protected shields have limited advantage in preventing dental injuries during intubation. The shields cover the maxillary incisors, yet provide only limited protection for the teeth. Such shields are prone to displacement by either the laryngoscope blade or other instrumentation. Furthermore, existing shields are relatively difficult to use, requiring multiple operator steps to secure the shields for use. The multiple steps required to secure existing shields may discourage their use by significantly increasing the time and effort required to achieve the desired intubation. Moreover, the bulk of the protective shields may obstruct the user's view into the hypopharynx.

U.S. Pat. No. 3,826,248 to Gobels presents a laryngoscope blade in which an elastic insert which is anchored within a mating opening in the tongue deflector by means of undercut grooves extending in cross and longitudinal directions relative to each other.

U.S. Pat. No. 4,583,527 to Musicant et al. teaches the placement of an elongated layer of soft, pliable plastic material which is adhere to the upper surface of a sheath which is slidably and removably coupled to the flange or curved edge of the tongue deflector of a laryngoscope blade.

U.S. Pat. No. 5,065,738 to Van Dam provides for a flexible padded sheath, which is adhered along the length of a laryngoscope blade, covering substantially its entire outer surface.

U.S. Pat. No. 5,438,976 to Nash provides a self-adherent, deformable cushioning device wrapped around a laryngoscope blade along at least a portion of its length.

U.S. Pat. No. 5,776,053 to Dragisic et al. provides a laryngoscope blade with a cutout or recess in the vertical portion of the tongue deflector where a resilient insert is removably coupled at its proximal and distal ends.

The devices currently available do not satisfactorily address the need to protect a patient's teeth, as well as the needs of convenience and feasibility of use. Blade covers are cumbersome and slow to apply to the blade, and are therefore impractical in emergency situations. Moreover, a cushioning device should be easy to remove after use and should not leave a permanent residue on the blade or the patient's teeth or mouth. While blade covers currently available are generally used only once, a typical laryngoscope blade is reusable and is commonly sterilized in steam autoclaves between uses. Adhesives used in applying a blade cover to a blade often make it difficult to remove the blade cover and may leave a residue that is difficult to remove. Adhesive residues may become even more difficult to remove after the residue has been subjected to the heat and pressure of the sterilization process. In addition, any such residue on a reusable instrument may present a potential focus for infectious bacteria or other pathogenic organisms. Further, blade covers that surround the entire blade or entire flange occupy too much space in a patient's mouth, making manipulation of the laryngoscope blade and introduction of the endotracheal tube difficult.

Common user errors during positioning of a laryngoscope, as well as the particular structure of a given blade, may cause difficulties in proper introduction of an endotracheal tube. Such errors, which include the placement of the blade at an improper depth and incomplete displacement of the tongue, may be more likely with one blade over another. For example, complete displacement of the tongue may be more difficult with blades styles wherein the flange curves back over the blade, presenting a relatively small passageway for the actual passage of an endotracheal tube.

SUMMARY OF THE INVENTION

The present invention is directed to a modified laryngoscope blade with a removable protective insert that is designed to reduce the risk of dental injuries in the course of endotracheal intubation in patients. The inventive blade is compatible with conventional laryngoscope handles, which provide both ergonomic and power supply functions. The inventive blade may be provided in both straight and curved embodiments, and may incorporate fiberoptic carriers, a distal miniature lamp for illumination, or other ancillary features whether visually oriented or not.

The modified blade corresponds to a conventional laryngoscope blade, with the addition of a cut-out area proximally with a channel sized and shaped to receive a removable protective insert. The blade portion of the present invention is substantially rigid, and is preferably constructed of a metal or metal alloy that is capable of withstanding repeated autoclave sterilizations for repeated use. Alternately, the blade may be constructed of a rigid plastic, or other material, and may be provided as a single-use, disposable unit.

In a preferred embodiment, the inventive modified blade provides a standard mechanical interface for a conventional laryngoscope handle, as well as standard electrical interfaces and wiring to a distal, miniaturized lamp for illumination. Alternately, fiberoptic illumination may be employed, using fiberoptic carriers within the modified blade that may be supplied by either an external light source, or by a conventional light source contained within a laryngoscope handle, or by an internal lamp housed proximally within the modified laryngoscope blade.

To minimize inadvertent displacement of the protective insert, the modified blade may also be provided with a spring-loaded pin, or other fastener that may engage a receptacle on the insert when an insert is slid into position for use. Alternately, the modified blade may incorporate such a receptacle in the path of a spring-loaded pin or other fastener located within the insert, to similarly secure the insert during use. In various embodiments of the present invention, the spring-loaded pin may be operated by a coiled spring, or by a non-coiled spring. In each of the various embodiments of the present invention, the protective insert may be quickly and easily secured in its operative position, requiring minimal additional operator time as compared with a conventional laryngoscope blade.

The protective insert is preferably constructed of a resilient material, capable of compression, and yet capable of maintaining its basic structural form. Preferably, the protective insert would be supplied as a disposable, single-use item. The protective insert is preferably shaped to provide surface continuity with the inventive modified blade when the insert is secured in position for use. Furthermore, the protective insert can preferably be sized and configured to produce no greater bulk that might obstruct either the user's visual field or working access, distal to the zone of the insert during an intubation procedure. Finally, the insert preferably has a slidable blade connector to engage with a channel on the modified blade to position the insert. In addition, the insert may be provided with either a receptacle to receive a spring-loaded pin from the modified blade to lock the insert in position during use, or alternately the insert may contain such a spring-loaded pin that might engage with a receiving interface on the modified blade. The inventive design also preferably allows a limited amount of front-to-back motion within the context of the locking spring-loaded pin/receptacle system, to minimize further shear forces that might otherwise be transmitted to the patient's teeth or alveolar ridges.

OBJECTS OF THE INVENTION

As discussed above, there remains a need to further reduce the likelihood of trauma to which all of the mouth and throat are exposed during the technique of tracheal intubation. Therefore, one object of the present invention is to provide a device to allow intubation while adequately protecting the teeth, tongue, and oral mucosa from the blade of a laryngoscope during orotracheal or direct nasotracheal intubation.

As clinicians often have personal preferences as to the style of laryngoscope blade that they routinely employ for intubation, another object of the present invention is to provide a device that may be employed to protect the teeth, tongue and oral mucosa for all types of laryngoscope blades, whether the blades are curved, straight, or partially curved.

Still another object of the present invention is to provide a method for carrying out the technique of intubation whereby the teeth, tongue, and oral mucosa are protected from iatrogenic trauma.

Still another object of the present invention is to provide a device that will permit rapid and easy protection of the teeth, tongue, and oral mucosa from the blade of a laryngoscope during intubation, while requiring minimal additional actions on the part of the user/operator. These and other objects will be better understood when the device and method of the present invention are described in the detail of the preferred embodiment and particularly pointed out and distinctly claimed in the claims.

DETAILED DESCRIPTION OF EXEMPLARY EMBODIMENTS

Figure 1:
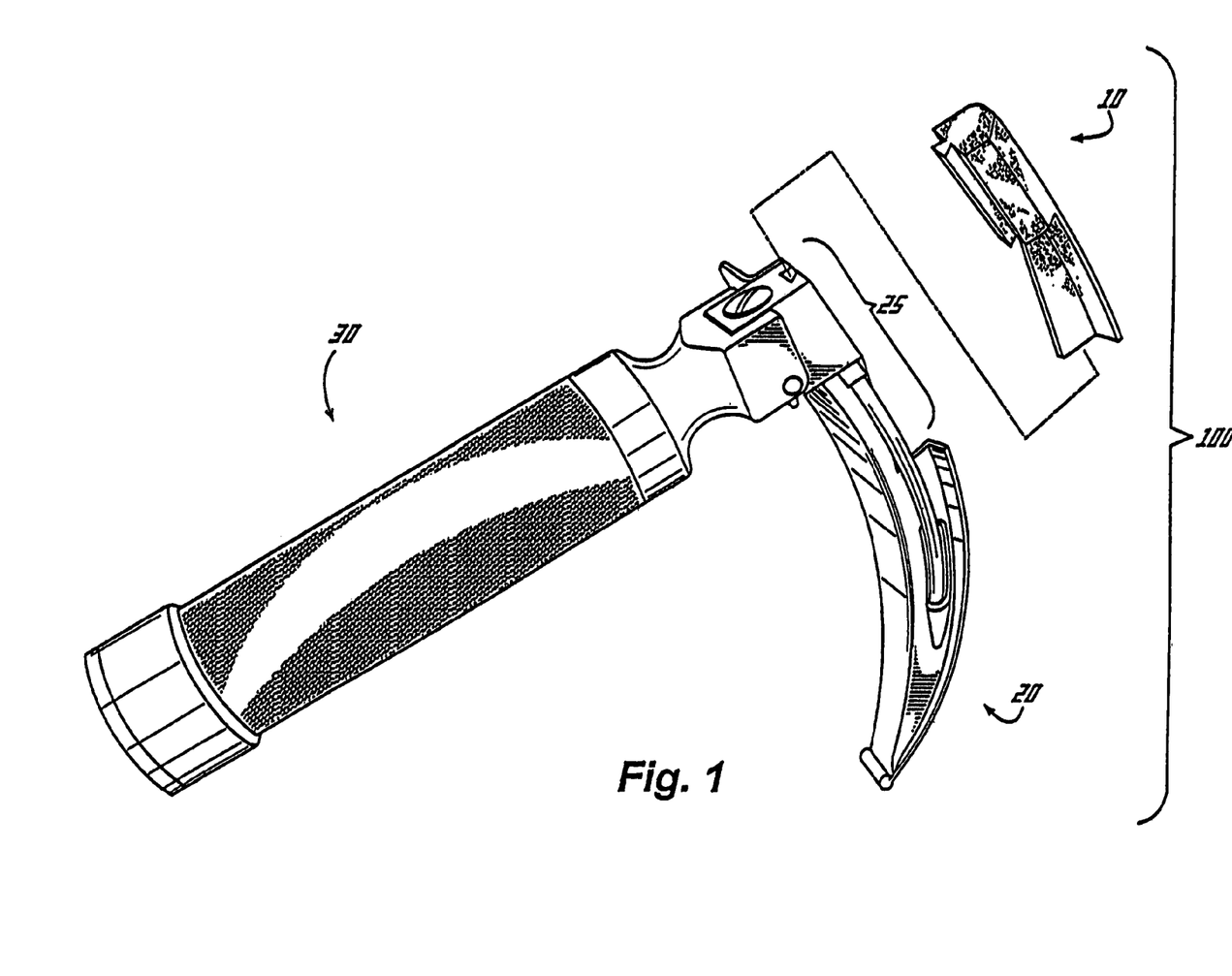
FIG. 1 shows a partially exploded view of a first embodiment of a modified laryngoscope blade and a removable protective insert according to the present invention.

An overview of a preferred embodiment of the present invention is illustrated in FIG. 1. The inventive modified laryngoscope blade assembly 100 includes a removable protective insert 10 and a modified blade structure 20. The blade structure 20 has a recess 25 in its upper surface into which the insert 10 is received. The inventive modified laryngoscope blade assembly 100 is designed to functionally mount on a conventional laryngoscope handle 30 which serves both as a user handle and as a battery housing and power supply.

Figure 2:
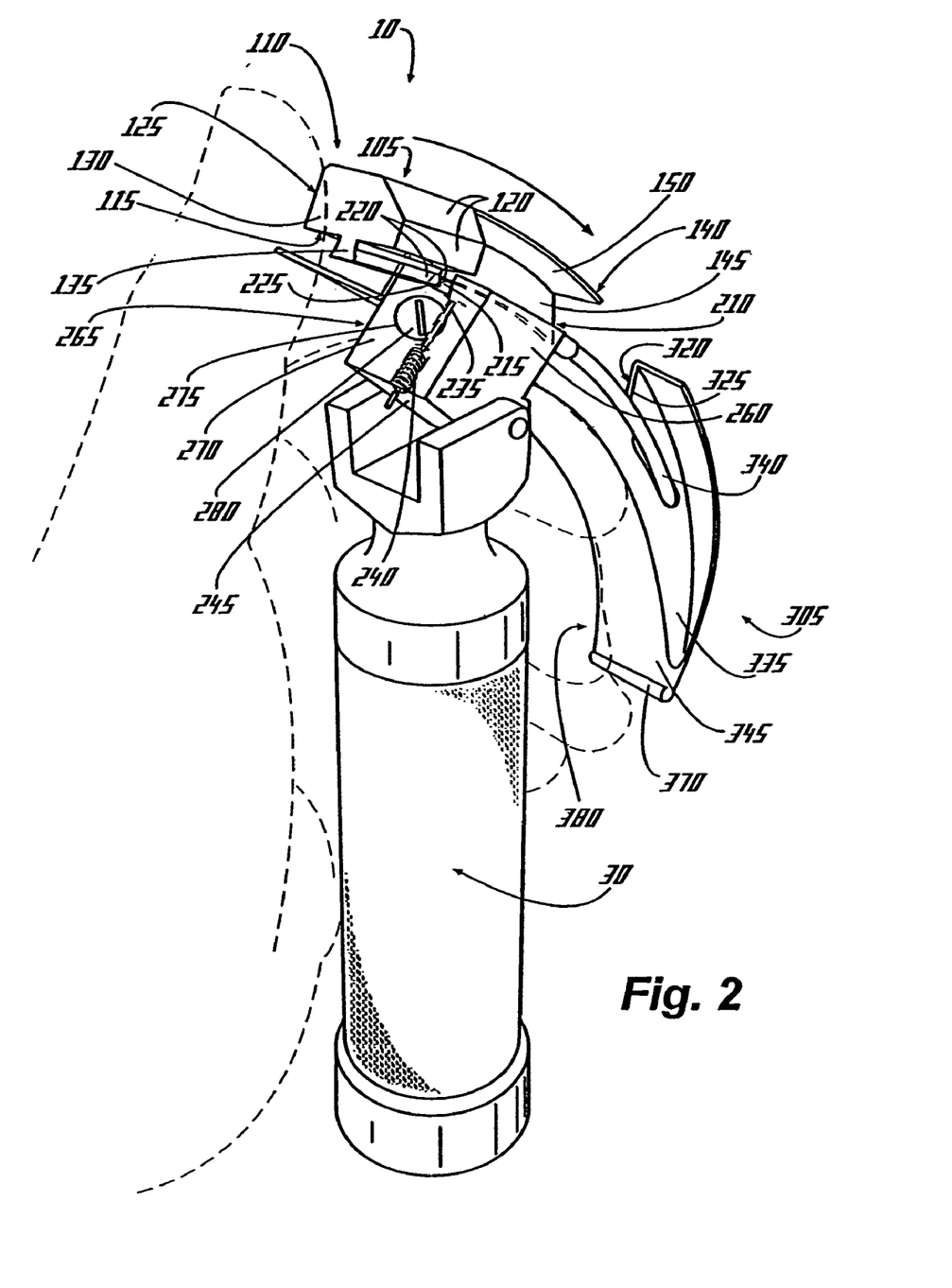
FIG. 2 shows the insertion of the insert of FIG. 1 into the receiving channel of the blade of FIG. 1.

FIG. 2 provides further details of the working interaction among the removable protective insert 10, the modified blade structure 20, and the conventional laryngoscope handle 30 of FIG. 1. The protective insert 10 has a body portion 105 and a blade portion 145. The body portion 105 has an maxillary surface 110, a blade interface surface 115, a buccal surface 120, a medial surface 125, an anterior surface 130, and a retention ridge 135. The retention ridge 135 extends along the long axis of the blade interface surface 115 of the body portion 105. The retention ridge 135 in this embodiment of the present invention is slightly wedge-shaped, with a narrower attachment to the body portion 105 and a broader base at its free edge. The buccal surface 120 may be a vertical planar component, or it may be beveled or rounded in various embodiments of the present invention.

The blade portion 145 of the insert 10 consists of a vertical blade 150, a palatal blade 155, and a distal edge 160.

According to the present invention, the protective insert 10 is preferably constructed of a resilient, pliable material that would maintain its structural integrity, but would absorb and diffuse mechanical stress that might be imparted to the teeth or other body structures at risk with a completely rigid blade. Resilience in the context of the present invention is a quality of the construction or composition of the protective insert 10 that allows the protective insert 10 to provide a cushioning effect to adjacent structures. More preferably, the protective insert 10 according to the present invention provides a cushioning structure which is compressible when mechanical force is applied, yet capable of elastic reformation upon relaxation of the compressing force. Most preferably, the protective insert 10 according to the present invention has sufficient elasticity to provide a localized cushioning effect while possessing sufficiently firm durometer strength to substantially maintain its basic shape and form.

A protective insert 10 according to the present invention would be capable of withstanding sterilization by irradiation, gas or chemical agents, or steam autoclave exposure without suffering structural degradation.

A protective insert 10 according to the present invention may be formed of a solid structure. Alternately, a protective insert 10 according to the present invention may be formed of a laminar, foam, matrix, or partially hollow structure. In a protective insert 10 according to the present invention may be formed of a the protective insert 10 may be constructed of rubber, plastic, or other polymers. In a more preferred embodiment of a protective insert 10 according to the present invention, the insert 10 may be formed of materials selected from the group of natural or synthetic rubbers, elastomers, polyisoprenes, polyurethanes, vinyl plastisols, acrylic polyesters, polyvinylpyrrolidone-polyurethane interpolymers, butadiene rubbers, styrene-butadiene rubbers, rubber lattices, and other polymers or materials with similar resilience and pliability qualities.

In a preferred embodiment of the present invention, the protective insert 10 may be fabricated by a molding process. Alternately, the protective insert 10 may be fabricated by machining the finished form of the insert 10 from a block of raw material. In a more preferred embodiment according to the present invention, the protective insert 10 may be fabricated by an extrusion molding process. Most preferably, an embodiment of the protective insert 10 may be formed by injection molding, according to the present invention. In a preferred embodiment of the present invention, the protective insert 10 may be fabricated with a surface coating to reduce water absorption and surface friction along the exposed surfaces of the insert 10. In yet another preferred embodiment of the present invention, the protective insert 10 may be fabricated without a surface coating over the exposed surfaces of the insert 10.

In a preferred embodiment according to the present invention, the protective insert 10 would be supplied as a sterile packaged, disposable item for single use. In an alternate preferred embodiment, the protective insert 10 would be constructed to resist degradation from repeated gas, chemical, or steam autoclave sterilization exposures.

The modified blade structure 20 includes a blade body portion 205 and a blade portion 305. The blade body portion 205 includes a maxillary surface 210, a handle interface facet 245, a buccal surface 260, a medial surface 265, an anterior surface 270, and a posterior facet. The maxillary surface 210 further contains a retention channel 215, defined by side walls 220 and a floor 225.

Figure 3:
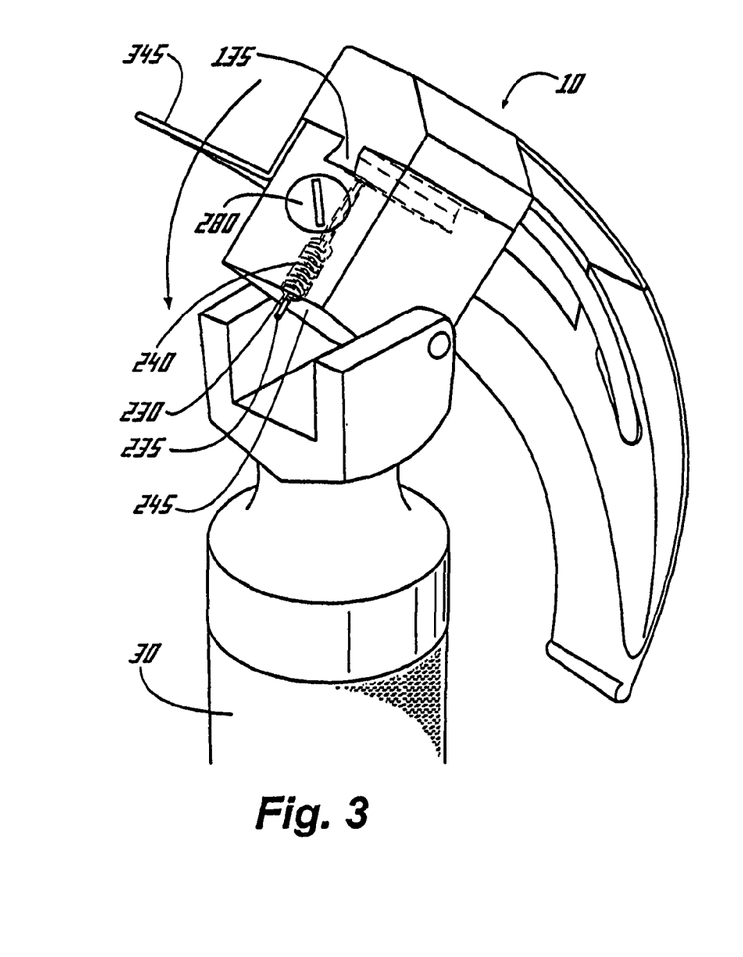
FIG. 3 shows the pivoting mounting of the blade assembly of FIG. 1 onto the receiving connector of a conventional laryngoscope handle.
Figure 4:
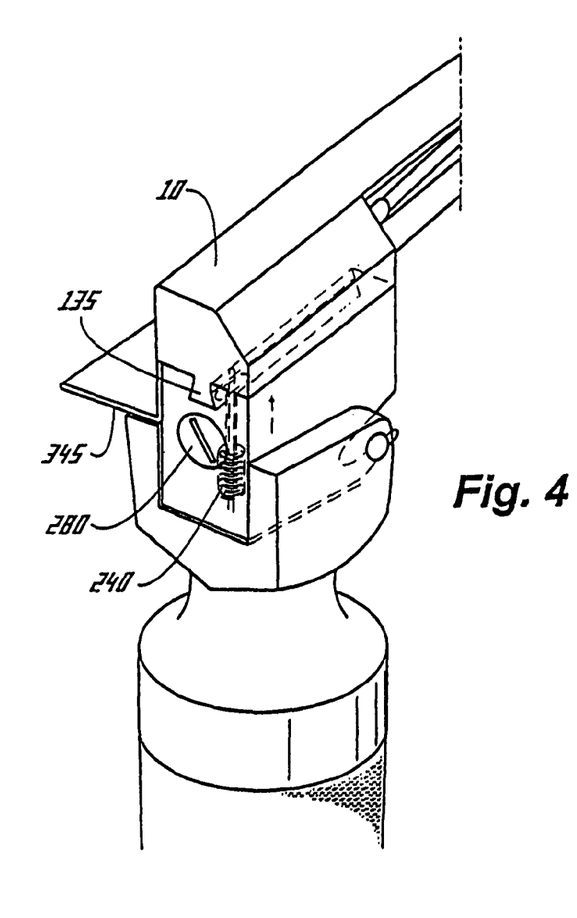
FIG. 4 shows the relationship between the blade assembly of FIG. 1 and a conventional laryngoscope handle, with the blade in a fixed and extended position for use.

As shown in FIGS. 2–3, when the blade structure 20 is mounted atop the handle 30, but not extended into a locked position for use, the protective insert 10 is freely slidable, with the retention ridge 135 of the insert 10 sized to be received by the retention channel 215 of the blade body portion 205. However, the floor 225 of the retention channel 215 may also be provided with a vertical bore 230 that contains a retention pin 235 that protrudes from the surface of the handle interface facet 245 under tension from a spring 240 also contained within the bore 230. As shown in FIG. 4, the retention pin 235 may be compressed into the blade body portion 205 under tension from the spring 240 when the blade assembly 100 is locked into an extended position on the handle 30. When the lower end of the retention pin 235 is compressed into the blade body portion 205 by the locking, pivoting action of the inventive laryngoscope blade assembly 100, the upper end of said pin 235 is pushed through the bore 230 and extended through the surface plane of the maxillary surface 210 of the blade body portion 205, and into a pin receptacle 140 provided in the lower edge of the retention ridge 135 of the insert 10. This has the effect of mechanically engaging and securely locking the insert 10 onto the blade assembly 20.

The action of securing the insert 10 onto the blade assembly 20 thus occurs as a result of the mechanical action of engaging the blade assembly 20 with the laryngoscope handle 30. Therefore, in a preferred embodiment of the present invention, only the additional step of sliding the protective insert 10 onto the blade assembly 20 is required of the user, and the position of the insert 10 is automatically secured when the blade assembly 20 is engaged in an extended position on the handle 30.

In the preferred embodiment, the pin receptacle 140 may be elongate or elliptical, rather than round in shape, and oriented to allow slight front-to-back motion while the pin 235 is in position within the insert 10. The slight motion that is thus allowed is designed to prevent shear stress from being transmitted to the patient's upper incisor teeth, and further reduces the risk of attendant dental injuries. In an alternate embodiment of the present invention, however, where slight front-to-back motion is not desired, the pin receptacle 140 may be round to exactly receive the pin 235.

The anterior surface 270 may contain a central threaded bore 275 which may be enclosed by a set screw 280. Depending upon the mode of illumination used in the given embodiment, the threaded bore 275 provides access either to electrical conduits (not shown) which may extend to a conventional distal lamp, or the threaded bore 275 may provide access to a conventional lamp and lamp socket (also not shown) within the blade body portion 205 with a conventional fiberoptic carrier extending distally through said bore 275 from said lamp to a terminal point (not shown).

Figure 5:
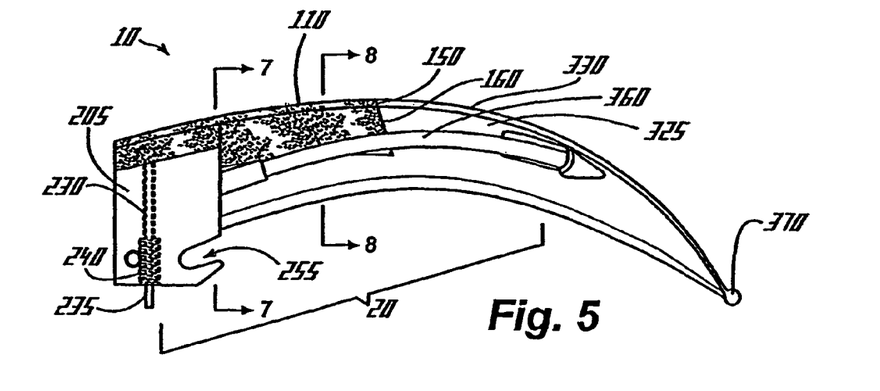
FIG. 5 shows a side view of the lateral surface of the blade assembly of FIG. 1.

FIG. 5 shows details of the buccal, or lateral side view of the inventive blade assembly 100 of FIG. 1. The insert 10 is shown fully seated into the recess 25 in the blade structure 20. The distal edge 160 of the vertical blade portion 150 is flushly abutted with the corresponding edge of the vertical blade 325 of the blade structure 20. Also, the maxillary or upper surface 110 of the removable protective insert 10 is substantially flush with the upper surface 330 of the modified blade structure 20.

The illumination conduit 360 extends from the blade body portion 205 of the blade structure 20 to the illumination tip 370. Laryngoscopes require some internal means of illumination to allow vision in the recesses of the pharynx and larynx. Typically, laryngoscopes may include a miniature lamp which is located on the laryngoscope blade, or a fiberoptic carrier may be provided to transmit light from a source either within the handle or from an external light source to the distal aspect of the laryngoscope blade.

In various preferred embodiments of the present invention, either a distal conventional lamp or a conventional fiberoptic carrier may be provided for illumination on the modified laryngoscope blade. As previously stated, the illumination conduit 360 may either contain electrical leads for a lamp (not shown) located in said illumination tip 370, or the illumination conduit may contain fiberoptic carriers extending to the tip 370 from a lamp (not shown) housed within the blade body portion 205, or from an external light source.

The blade portion 205 is further provided with an engagement hook 255, sized and positioned to engage the pivot pin of a standard laryngoscope handle 30.

Unlike the protective insert 10 which is preferably constructed of a resilient material, in a preferred embodiment according to the present invention, the blade structure 20 is substantially rigid to allow adequate physical retraction of anatomic structures for proper use. In a more preferred embodiment of the present invention, the blade structure 20 is constructed of metal or metal alloys. In another, more preferred embodiment, the blade structure 20 is constructed of rigid plastics. Most preferably, the blade structure 20 is constructed of stainless steel or aluminum. In a preferred embodiment of the present invention, a blade structure 20 might either be provided in a straight or curved configuration.

FIG. 5 further shows the relationships among the vertical bore 230 for the retention pin 235 and tension spring 240 within the blade body portion 205 of the blade structure 20 of FIG. 1.

Figure 6:
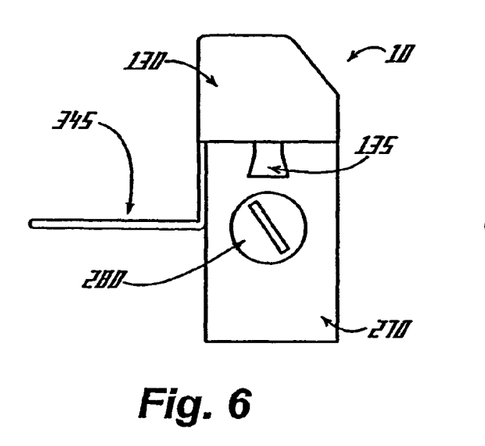
FIG. 6 shows the anterior surface of the blade assembly of FIG. 1.
Figure 7:
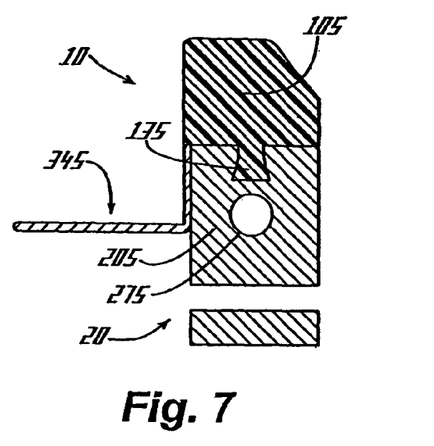
FIG. 7 shows a cross-sectional view of the blade assembly of FIG. 1 across the plane 7–7' on FIG. 5.

FIG. 6 shows the anterior aspect of the inventive laryngoscope 100 of FIG. 1, with a tongue deflector 345 extending medially from the blade structure 20, and with the insert 10 and the retention ridge 135 in position. The anterior surface 270 contains the set screw 280 which provides access within as described above FIG. 7 shows a cross-sectional view through the inventive laryngoscope blade assembly 100 through the plane 7–7' on FIG. 5. This further shows the retention ridge 135 in position within the body 205 of the blade portion 20, as well as the relationship of the bore 275 within said body 205. At the level shown in this cross-sectional drawing, both the insert 10 and the blade structure 20 are relatively thick in their cross-sectional area, thus imparting a great deal of structural strength to this portion of the overall inventive laryngoscope blade assembly 100. The broadness of the insert 10 at this level further diffuses any physical stress that might be imparted to the patient's teeth at the point where maximal contact between the teeth and the inventive blade assembly 100 might be expected.

Figure 8:
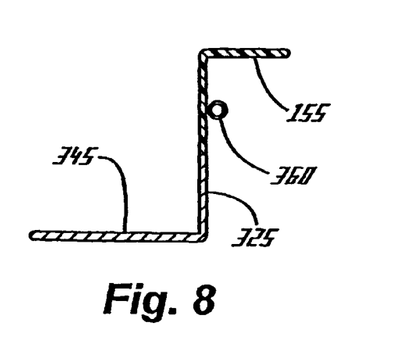
FIG. 8 shows a cross-sectional view of the blade assembly of FIG. 1 across the plane 8–8' on FIG. 5.

FIG. 8 shows a cross-sectional view through the inventive laryngoscope blade assembly 100 through the plane 8–8' on FIG. 5. This shows the seamless junction of the vertical blade 150 of the insert 10 and the vertical blade 325 of the blade structure 20. It should be noted that both the vertical blade 150 of the insert 10 and the vertical blade 325 of the blade structure 20 are relatively thin at this level, minimizing both mechanical and visual obstruction for the user who must both inspect the larynx distal to this level and be able to pass an endotracheal tube or other instrumentation around the inventive laryngoscope blade 100 at or below the level shown. However, despite the thin structure, the palatal blade 155 of the insert 10 provides a broad, resilient surface to reduce the injury potential along the course of the device which might contact the delicate palate or oropharyngeal mucosal surfaces.

Figure 9:
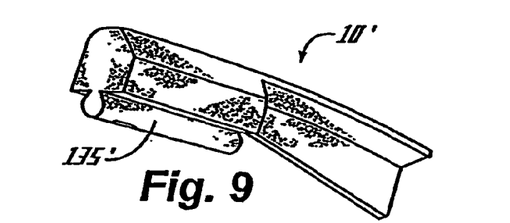
FIG. 9 shows an alternative embodiment of a protective insert according to the present invention in which the retention ridge on the blade interface surface is cylindrical and attached to the blade interface surface along one edge of the longitudinal axis of the retention ridge.
Figure 10:
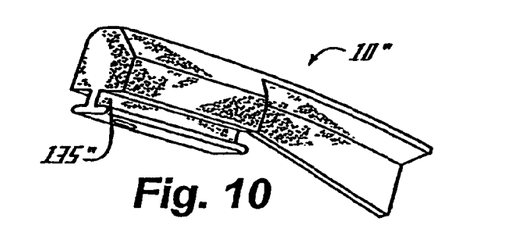
FIG. 10 shows another alternative embodiment of a protective insert in which the retention ridge on the blade interface surface is T-shaped and attached to the blade interface surface by the vertical portion of the T-shaped ridge.

FIGS. 9–10 show alternate embodiments of the inventive insert 10' and 10" components, in which the retention ridges 135' and 135" might be provided in a rounded (FIG. 9) or T-shaped (FIG. 10) configuration, with corresponding changes in the retention channels of the blade body portions in such embodiments (not shown). Such embodiments would preserve the slidably removable quality of the inserts 10' and 10", as well as their interactions with the blade assemblies 20.

Figures 11, 12:
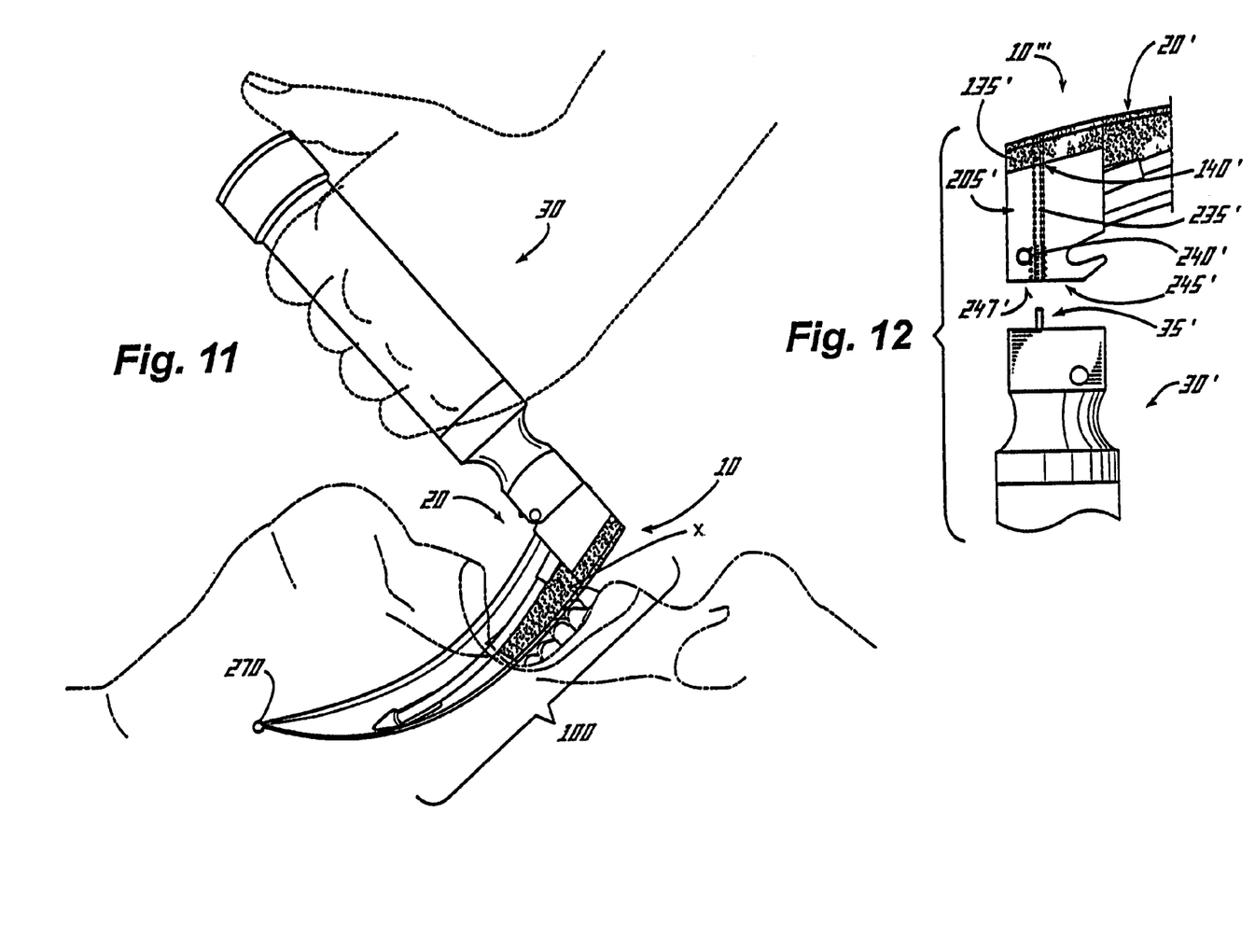
FIG. 11 shows a side view of the anatomic relationship of the laryngoscope blade assembly of FIG. 1 in clinical use for intubation of a patient.
FIG. 12 shows another alternative embodiment of the present invention, in which a fixed pin on the laryngoscope handle is received by a bore on the laryngoscope blade assembly, and in turn displaces a spring-loaded pin within the blade assembly to secure an attached protective insert.

FIG. 11 shows a cross-sectional view of the anatomic relationships of the inventive laryngoscope blade 100 of FIG. 1 in use to visualize a patient's larynx. The user is typically working from a position above the head of a supine patient. For a right-handed user, the handle 30 is usually held vertically in the left hand, with the laryngoscope blade 100 oriented downwards and away from the user. The blade 100 is introduced into the patient's mouth, and the distal tip 270 is advanced into the pharynx, displacing the tongue anteriorly and to the left. The larynx is visualized off the medial side of the laryngoscope blade 100, and the endotracheal tube or other instruments are introduced along the medial side of said blade 100. In the course of insertion, or in the position of use, the laryngoscope blade 100 may contact or nearly contact the patient's upper incisor teeth at the point indicated as X on FIG. 11. This point of contact is within the insert 10 portion of the blade 100, and is away from the rigid blade structure 20, thus protecting the patient's teeth and other delicate oral structures from inadvertent injury during the procedure.

As can be seen in FIGS. 3, 5, and 1, when the insert 10 is positioned within the recess 25 in the modified blade structure 20, the upper or maxillary surface 110 of the insert 10 and the upper surface 330 of the modified blade structure 20 form a substantially continuous upper surface. That is, the upper or maxillary surface 110 does not project above the adjacent upper surface 330 of the blade structure 20. The insert 10 thus does not increase the profile of the laryngoscope system and therefore does not interfere with the intubation process any more than a conventional laryngoscope.

FIG. 12 shows a side view of yet another alternative embodiment of the present invention, in which the laryngoscope handle 30' is provided with a fixed pin 35' which may be received by an appropriately-sized bore 247' in the handle interface facet 245' of the blade structure 20'. In this embodiment, the entry of the fixed pin 35' into bore 247' acts to mechanically displace the retention pin 235' that is enclosed under tension of a spring 240' within a vertical bore 230' that is located within the blade body portion 205', and is continuous therein with bore 247'. The displacement of the retention pin 235' by the fixed pin 35' as described serves to extend the opposite end of said retention pin 235' into a pin receptacle 140' provided in the lower edge of the retention ridge 135' of the protective insert 10'''. This has the effect of securely locking the insert 10''' into the blade assembly 20'. As discussed previously, the pin receptacle 140' may be elongated or elliptical, rather than round in shape, and oriented to allow slight front-to-back motion while the retention pin 235' is in position within the insert 10'''.

Although the foregoing embodiments of the present invention have been described in some detail by way of illustration and example for purposes of clarity and understanding, it will be apparent to those skilled in the art that certain changes and modifications may be practiced within the spirit and scope of the present invention. Therefore, the description and examples presented herein should not be construed to limit the scope of the present invention, the essential features of which are set forth in the appended claims.

We claim:

1. A laryngoscope, comprising: an elongated handle having an upper portion; a blade structure mounted to said upper portion of said handle, said blade structure extending substantially transverse to said handle, said blade structure being configured on one end to engage and to retract anatomical structures, said blade structure having an upper surface, and said blade structure further defining a recess in said upper surface with a retention channel therein; an at least partially resilient insert received within said recess in said upper surface of said blade structure, said insert having an upper surface, and said upper surface of said blade structure and said upper surface of said insert defining a substantially continuous contour; said at least partially resilient insert further having a retention ridge; said at least partially resilient insert being removably attached to said blade structure by engagement of said retention ridge and said retention channel along a substantial portion of said recess.

2. The laryngoscope of claim 1, wherein said at least partially resilient insert is removably attached to said blade structure by way of means operatively associated with said recess and said insert for removably engaging said insert with said blade structure.

3. The laryngoscope of claim 1, wherein said means operatively associated with said recess and said insert for removably engaging said insert with said blade structure comprises: a retention channel formed on one of said insert and said blade structure, and a mating retention ridge formed on the other of said insert and said blade structure and configured to slidably engage said retention channel on the one of said insert and said blade structure.

4. The laryngoscope of claim 3, wherein said retention channel formed on said blade structure is open at the top, wherein said retention channel has a base, and wherein said top of said retention channel is narrower than said base; and wherein said retention ridge of said insert is narrower at its line of attachment to the insert and broader at its free edge.

5. The laryngoscope of claim 3, wherein said retention channel formed on said blade structure is substantially oval, with a major portion of said retention channel being wider than the opening of the retention channel, and wherein said retention ridge is substantially oval, with a major portion of said retention ridge being wider than a line of attachment of said retention ridge to said insert.

6. The laryngoscope of claim 3, wherein said retention channel is shaped like an inverted "T", and wherein said retention ridge is shaped like an inverted "T".

7. The laryngoscope of claim 3, wherein said blade structure is pivotably mounted to said handle for movement between a first position in which said blade structure is substantially transverse to said handle and a second position in which said one end that engages and retracts anatomical structures is displaced downward, wherein said handle further comprises a pin operatively associated with said upper portion thereof, said pin extending through a hole in said blade structure and blocking said retention channel when said blade structure is in said first position, and said blade structure rotating so as to clear said retention channel from said pin when said blade structure is in said second position; and wherein said insert has a hole formed in a lower portion thereof dimensioned to receive said pin therewithin when said blade structure is rotated to said second position, said insert is inserted into said retention channel, and said blade structure returned to said first position, whereby said pin engaging said hole in said insert locks said insert in place.

8. The laryngoscope of claim 1, wherein said upper surface of said blade structure and said upper surface of said insert form a substantially continuous curved upper surface.

9. The laryngoscope of claim 1, wherein the portion of said insert that is inserted into said recess first has top and side contours that correspond with the adjacent mating portion of said blade structure.

10. An apparatus for use with an elongated laryngoscope handle having an upper portion, said apparatus comprising: a blade structure pivotably mountable to said upper portion of said elongated laryngoscope handle, said blade structure when so mounted to said upper portion of said elongated laryngoscope handle extending substantially transverse to said handle, said blade structure being configured on one end to engage and to retract anatomical structures, said blade structure having an upper surface, and said blade structure further defining a recess in said upper surface with a retention channel therein; an at least partially resilient insert received within said recess in said upper surface of said blade structure, said insert having an upper surface, and said upper surface of said blade structure and said upper surface of said insert defining a substantially continuous contour; said at least partially resilient insert further having a retention ridge; said at least partially resilient insert being removably attached to said blade structure by engagement of said retention ridge and said retention channel along a substantial portion of said recess.

11. The apparatus of claim 10, wherein said at least partially resilient insert is removably attached to said blade structure by way of means operatively associated with said recess and said insert for removably engaging said insert with said blade structure.

12. The apparatus of claim 10, wherein said means operatively associated with said recess and said insert for removably engaging said insert with said blade structure comprises: a retention channel formed on one of said insert and said blade structure, and a mating retention ridge formed on the other of said insert and said blade structure and configured to slidably engage said retention channel on the one of said insert and said blade structure.

13. The apparatus of claim 12, wherein said retention channel formed on said blade structure is open at the top, wherein said retention channel has a base, and wherein said top of said retention channel is narrower than said base; and wherein said retention ridge of said insert is narrower at its line of attachment to the insert and broader at its free edge.

14. The apparatus of claim 12, wherein said retention channel formed on said blade structure is substantially oval, with a major portion of said retention channel being wider than the opening of the retention channel, and wherein said retention ridge is substantially oval, with a major portion of said retention ridge being wider than a line of attachment of said retention ridge to said insert.

15. The apparatus of claim 12, wherein said retention channel is shaped like an inverted "T", and wherein said retention ridge is shaped like an inverted "T".

16. The apparatus of claim 12, wherein said blade structure is pivotably mountable to said handle for movement between a first position in which said blade structure is substantially transverse to said handle and a second position in which said one end that engages and retracts anatomical structures is displaced downward, wherein said handle further comprises a pin operatively associated with said upper portion thereof, said pin extending through a hole in said blade structure and blocking said retention channel when said blade structure is mounted to said handle and is in said first position, and said blade structure rotating so as to clear said retention channel from said pin when said blade structure is mounted to said handle and is in said second position; and wherein said insert has a hole formed in a lower portion thereof dimensioned to receive said pin therewithin when said blade structure is mounted to said handle and is rotated to said second position, said insert is inserted into said retention channel, and said blade structure returned to said first position, whereby said pin engaging said hole in said insert locks said insert in place.

17. The apparatus of claim 10, wherein said upper surface of said blade structure and said upper surface of said insert form a substantially continuous curved upper surface.

18. The apparatus of claim 10, wherein the portion of said insert that is first inserted into said recess has top and side contours that correspond with the adjacent mating portion of said blade structure.

19. A device for use with a laryngoscope having an elongated handle with an upper portion, a blade structure pivotably mounted to said upper portion of said handle, said blade structure extending substantially transverse to said handle, said blade structure being configured on one end to engage and to retract anatomical structures, said blade structure having an upper surface, and said blade structure further defining a recess in said upper surface with a retention channel therein, said device comprising: an at least partially resilient insert configured to be received within said recess in said upper surface of said blade structure, said insert having an upper surface, and said insert being configured such that when said insert is received within said recess, said upper surface of said blade structure and said upper surface of said insert define a substantially continuous contour; said at least partially resilient insert further having a retention ridge; said at least partially resilient insert being removably attachable to said blade structure by engagement of said retention ridge and said retention channel along a substantial portion of said recess.

20. The device of claim 19, wherein said at least partially resilient insert is removably attachable to said blade structure by way of means operatively associated with said recess and said insert for removably engaging said insert with said blade structure.

21. The device of claim 19, wherein said means operatively associated with said recess and said insert for removably engaging said insert with said blade structure comprises: a retention channel formed on one of said insert and said blade structure, and a mating retention ridge formed on the other of said insert and said blade structure and configured to slidably engage said retention channel on the one of said insert and said blade structure.

22. The device of claim 21, wherein said retention channel formed on the one of said insert and said blade structure is open at the top, wherein said retention channel has a base, and wherein said top of said retention channel is narrower than said base; and wherein said retention ridge formed on the other of said insert and said blade structure is narrower at its line of attachment to the insert and broader at its free edge.

23. The device of claim 21, wherein said retention channel formed on the one of said insert and said blade structure is substantially oval, with a major portion of said retention channel being wider than the opening of the retention channel, and wherein said retention ridge formed on the other of said insert and said blade structure is substantially oval, with a major portion of said retention ridge being wider than a line of attachment of said retention ridge to said other of said insert and said blade structure.

24. The device of claim 21, wherein said retention channel is shaped like an inverted "T", and wherein said retention ridge is shaped like an inverted "T".

25. The device of claim 21, wherein said blade structure with which said device is intended for use is pivotably mounted to said handle for movement between a first position in which said blade structure is substantially transverse to said handle and a second position in which said one end that engages and retracts anatomical structures is displaced downward, and wherein said handle with which said device is intended for use further comprises a pin operatively associated with said upper portion thereof, said pin extending through a hole in said blade structure and blocking said retention channel when said blade structure is in said first position, and said blade structure rotating so as to clear said retention channel from said pin when said blade structure is in said second position; and wherein said insert has a hole formed in a lower portion thereof dimensioned to receive said pin therewithin when said blade structure is rotated to said second position, said insert is inserted into said retention channel, and said blade structure returned to said first position, whereby said pin engaging said hole in said insert locks said insert in place.

26. The device of claim 19, wherein said upper surface of said blade structure and said upper surface of said insert form a substantially continuous curved upper surface.

27. The device of claim 19, wherein the portion of said insert that is inserted into said recess first has top and side contours that correspond with the adjacent mating portion of said blade structure.

* * * * *